(12) United States Patent  (10) Patent No.: US 8,950,027 B2
Yamamoto et al.  (45) Date of Patent: Feb. 10, 2015

(54) RESPIRATORY TRACT WIDENING TOOL AND RESPIRATORY TRACT WIDENING UNIT PROVIDED THEREWITH

(75) Inventors: Keiichi Yamamoto, Osaka (JP); Yuzuru Kitahara, Osaka (JP); Yasuyo Maruyama, Toyohashi (JP); Toru Shinzato, Nagoya (JP)

(73) Assignees: Fuso Pharmaceutical Industries, Ltd., Osaka (JP); Nextier, Aichi (JP)

( * ) Notice: Subject to any disclaimer, the term of this patent is extended or adjusted under 35 U.S.C. 154(b) by 299 days.

(21) Appl. No.: 13/518,140

(22) PCT Filed: Dec. 21, 2010

(86) PCT No.: PCT/JP2010/072968
§ 371 (c)(1),
(2), (4) Date: Sep. 28, 2012

(87) PCT Pub. No.: WO2011/078150
PCT Pub. Date: Jun. 30, 2011

(65) Prior Publication Data
US 2013/0025058 A1  Jan. 31, 2013

(30) Foreign Application Priority Data
Dec. 21, 2009 (JP) ................................. 2009-289497

(51) Int. Cl.
*A61F 5/56* (2006.01)

(52) U.S. Cl.
USPC .................................................. 5/640; 5/636

(58) Field of Classification Search
USPC ..................................... 5/612–622, 636–640
See application file for complete search history.

(56) References Cited

U.S. PATENT DOCUMENTS

| 4,285,081 A * | 8/1981 | Price .................................. 5/637 |
| 2006/0040104 A1 | 2/2006 | Wort et al. |
| 2010/0224198 A1 | 9/2010 | Ayuse et al. |

FOREIGN PATENT DOCUMENTS

| JP | 2000116662 A | 4/2000 |
| JP | 2006296640 A | 11/2006 |

* cited by examiner

*Primary Examiner* — Fredrick Conley
(74) *Attorney, Agent, or Firm* — MKG, LLC

(57) ABSTRACT

A respiratory tract widening tool capable of reliably managing a respiratory tract in a supine posture and freely changing the posture, and a respiratory tract widening unit provided therewith are provided.

8 Claims, 6 Drawing Sheets

(a)

(b)

(a)

(b)

(a)

(b)

(a)

(b)

RESPIRATORY TRACT WIDENING TOOL AND RESPIRATORY TRACT WIDENING UNIT PROVIDED THEREWITH

TECHNICAL FIELD

The present invention relates to a respiratory tract widening tool for respiratory tract management and a respiratory tract widening unit provided therewith.

BACKGROUND

Sleep apnea that repeats respiratory arrest lasting ten or more seconds a plurality of times during sleep is becoming problematic in recent years. When an apnea condition occurs, a thoracic cavity internal pressure becomes a strong negative pressure, blood accumulates in the thoracic cavity causing a high blood pressure, cardiac disease or the like or sleep is interrupted at deep third and fourth stages, and therefore people feel drowsiness during the daytime and might cause a traffic accident or the like. Sleep apnea is caused by a blockage of the upper respiratory tract, which is a passage of air, and attributable to fat deposition around the neck, tonsillar hypertrophy, micrognathia, falling of the root of tongue into the respiratory tractor the like.

Conventionally, respiratory tract management auxiliary apparatuses are known which are intended to prevent falling of the root of tongue. This respiratory tract management auxiliary apparatuses provided with a support section that stably supports the load of the lower jaw, a retractable leg that adjusts the distance from the support section to the position of the jaw to be supported, a jaw rest that is attached to the distal end of the leg and contacts and supports the human mandibular angle and an angle adjustment mechanism provided between the leg and the jaw rest.

SUMMARY

Technical Problem

When one keeps a supine posture for a long time during sleep, one's back is oppressed, the blood circulation of the back is impaired, and one-directional force is applied to the backbone or shoulder for a long time, causing shoulder stiffness or backache. To prevent this, people unconsciously toss and turn in bed, from a supine posture to a lateral position or from a lateral position to a supine posture a plurality of times during sleep.

However, when the above-described conventional respiratory tract management auxiliary apparatus is applied to sleep apnea prevention, this respiratory tract management auxiliary apparatus fixes the lower jaw with a jaw rest while keeping the support section stable, which results in a problem that people need to keep the supine posture and cannot change the direction of the body such as tossing and turning. That is, the conventional respiratory tract management auxiliary apparatus can secure the respiratory tract only when people are in a supine posture and keep a condition in which the lower jaw is completely fixed, and if, for example, people return to the supine posture again after tossing and turning during sleep, it is not possible to automatically manage the respiratory tract. Therefore, people need to stop sleeping once and fix the apparatus again every time people change the posture, which results in a problem of interrupting comfortable sleeping such as a reduction of sleeping time. Furthermore, when people are unaware that the apparatus comes off while sleeping, the respiratory tract is not managed in the supine posture and sleep apnea cannot be prevented.

The present invention has been implemented in view of the above-described problems and it is an object of the present invention to provide respiratory tract widening tool and a respiratory tract widening unit provided therewith capable of reliably managing the respiratory tract in a supine posture and easily changing the posture.

A respiratory tract widening tool of the present invention is a respiratory tract widening tool used attached to an outer periphery of the human neck, including: a main body that comes into contact with a posterior side of the neck when the tool is worn and receives an upward external force in a supine posture; and a pair of jaw retainers that extend forward from the main body spaced apart by a distance equivalent to the diameter of the neck and come into contact with both sides of the lower jaw when the tool is worn, and a protruding section that is provided in the main body and applies stress in a direction of pushing up the lower jaw in a supine posture to the main body, wherein: the main body and the pair of jaw retainers are formed of a restorable member, the main body and jaw retainers deform, when the posture is changed from the supine posture, in conformity with the posture, and when the posture is changed to the supine posture, the external force received by the main body is made to act on the jaw retainers to retain the lower jaw at a height at which the respiratory tract can be managed, and the main body includes a receiving face that is directly downward in a supine posture to press a tool underlay surface facing the neck and also receives a counterforce from the underlay surface.

According to this configuration, the main body receives an upward external force during the supine posture, the pair of jaw retainers that extend from the main body push up the lower jaw and retain the lower jaw at a height at which the respiratory tract can be managed, and it is thereby possible to prevent the root of tongue from falling into the throat side. That is, in the supine posture, the upward external force received by the main body is made to act on the pair of jaw retainers to keep the height of the lower jaw so that the height of the sub maxilla is not lowered due to relaxation of the neck muscle during sleep (during sound sleep). This prevents the root of tongue attached to the sub maxilla from falling into the throat side, and can thereby manage the respiratory tract. Furthermore, the main body and jaw retainers can be made of restorable members and the respiratory tract widening tool has a structure separated from a pillow or the like, and therefore when the posture is changed from a supine posture to a lateral position or a prone posture, the main body and jaw retainers deform according to the changed posture, and the user can thereby freely change the posture from the supine posture by tossing and turning. Furthermore, when the posture is returned to the supine posture, the main body receives an upward external force and the main body keeps the lower jaw at a height at which the respiratory tract can be managed, and can thereby automatically manage the respiratory tract again without interrupting comfortable sleeping.

According to this configuration, since the protruding section applies stress in the direction of pushing up the lower jaw to the main body, it is possible to enhance the effect that the upward bent respiratory tract is extended into a substantially rectilinear shape and sufficiently widen the respiratory tract.

According to this configuration, since the receiving face receives the counterforce from the underlay surface, the main body allows the counterforce to appropriately and uniformly apply to the pair of jaw retainers. Therefore, both lower jaws have a substantially identical height, that is, both sides of the lower jaw are kept at a height at which the respiratory tract can be managed in a stable condition without any one of the sides of the lower jaw being inclined. This allows the respiratory tract to be managed reliably.

A respitory tract widening tool of the present invention is a respitory tract widening tool used attached to an outer periphery of the human neck, including: a main body that comes into contact with a posterior side of the neck when the tool is worn and received an upward external force in a supine posture; and a pair of jaw retainers that extend forward from the main body spaced apart by a distance equivalent to the diameter of the neck and come into contact with both sides of the lower jaw when the tool is worn, wherein: the main body and the pair of jaw retainers are formed of a restorable member, the main body and jaw retainers deform, when the posture is changed from the supine posture, in conformity with the posture, and when the posture is changed to the supine posture, an external force received by the main body is made to act on the jaw retainers to retain the lower jaw at a height at which the respitory tract can be managed, the main body preferably includes a first main body that is connected to one of the jaw retainers and a second main body that is configured as a body independent of the first main body and connected to the other jaw retainer, and the pair of jaw retainers include adjusting means for adjusting an attaching position of the jaw retainers connected to the first and second main bodies with respect tooth sides of the lower jaw.

In this case, the main bodies connected to the respective jaw retainers are configured as independent bodies, and the user can thereby easily change the posture such as tossing and turning. Furthermore, since the attaching positions of the respective jaw retainers with respect to the lower jaw are adjusted according to the shape or the like of the lower jaw, even when, for example, the user returns to the supine posture after tossing and turning, it is possible to suppress deviations of the positions of contact of the jaw retainers with the lower jaw and retain the lower jaw at a height at which the respiratory tract can be managed appropriately.

A respiratory tract widening unit according tithe present invention is a respiratory tract widening unit including the above-described respiratory tract widening tool and a respiratory tract widening tool mat, wherein a head contacting section of the respiratory tract widening tool mat with which the head comes into contact in a supine posture is lower than a tool contacting section with which the main body of the respiratory tract widening tool comes into contact in the supine posture and the repertory tract widening tool mat is made up of a plurality of columnar bodies that are formed of a restorable elastic material and the columnar bodies vertically arranged in the head contacting section are lower than the columnar bodies vertically arranged in the tool contacting section.

According to this configuration, the head contacting section with which the head comes into contact in the supine posture is lower than the tool contacting section with which the main body comes into contact in the supine posture, and therefore the head is lower than the undersurface of the respiratory tract widening tool and the respiratory tract widening tool is relatively pushed up. That is, in the supine posture, in response to the sinking of the head downward, the respiratory tract widening tool relatively pushes up the lower jaw, and can thereby reliably suppress falling of the root of tongue and more reliably manage the respiratory tract.

Further according to this configuration, since the plurality of columnar bodies are made of a restorable elastic material, the region of the head contacting section is reliably distinguished from the region of the tool contacting section, it is possible to prevent the respiratory tract widening tool from sinking as the head sinks in the supine posture. Moreover, since the columnar body vertically arranged in the head contacting section is lower than the columnar body vertically arranged in the tool contacting section, the supine posture is set with the head and the respiratory tract widening tool aligned with the head contacting section and the tool contacting section respectively, the head naturally descends and the respiratory tract widening tool pushes up the lower jaw, and the respiratory tract can thereby be managed. Furthermore, when the posture is changed from the supine posture, the plurality of columnar bodies deform as the posture changes, and the user can thereby easily change the body position such as tossing and turning.

In the respiratory tract widening unit of the present invention, the elastic material may also be made of urethane resin.

Furthermore, in the respiratory tract widening unit, the respiratory tract widening tool mat is made up of a bag-shaped body filled with a gas, liquid or gel substance.

According to this configuration, when the head and respiratory tract widening tool come into contact with the respiratory tract widening tool mat, the head sinks more deeply than the respiratory tract widening tool due to the difference in weight, but the volume of the bag-shaped body itself does not change and the sinking of the respiratory tract widening tool is suppressed to an extent that the head sinks deeply. Therefore, the head naturally sinks in a supine posture and the respiratory tract widening tool pushes up the lower jaw, and therefore the respiratory tract can be managed.

According tithe present invention, it is possible to manage the respiratory tract in a supine posture and allow the user to easily change his/her posture during sleep.

DETAILED DESCRIPTION

Hereinafter, a respiratory tract widening tool and a respiratory tract widening unit according to embodiments of the present invention will be described in detail with reference tithe accompanying drawings. The respiratory tract widening unit according to the present embodiment is intended to manage the respiratory tract of people in a supine posture and is comprised of respiratory tract widening tool and a respiratory tract widening tool mat placed beneath the respiratory tract widening tool.

First Embodiment

First, the respiratory tract widening tool will be described.

Figure 1:
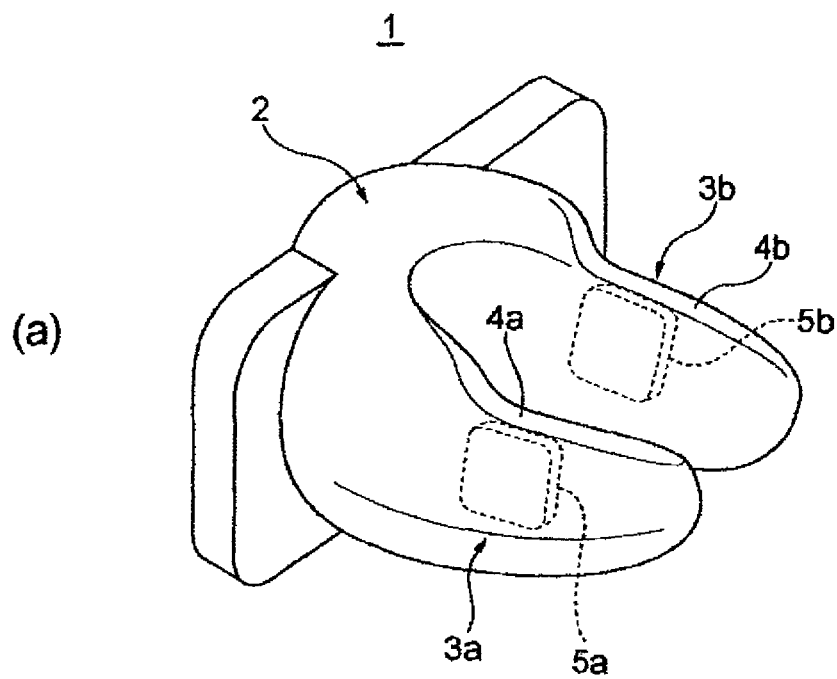
FIG. 1 is an outside perspective view schematically illustrating respiratory tract widening tool according to a first embodiment of the present invention, (a) is an outside perspective view seen from the front and (b) is an outside perspective view seen from thereof.
Figure 1:
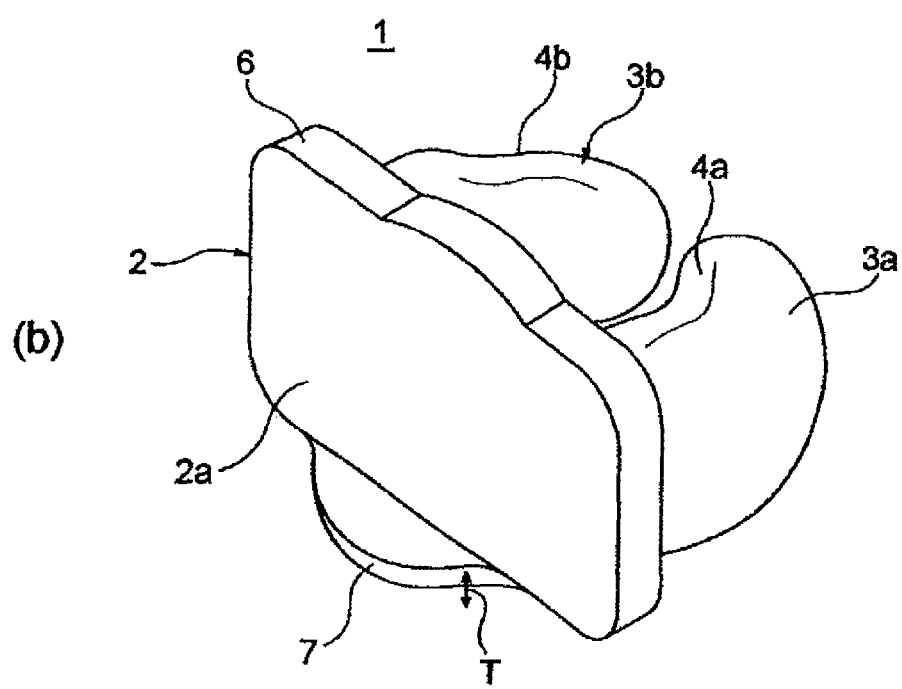

FIGS. 1(a) and (b) are outside perspective views of the respiratory tract widening tool according to a first embodiment of the present invention. The respiratory tract widening tool 1 is used attached to an outer periphery of the neck so as to cover the neck from behind the neck, and is provided with a main body 2 that comes into contact with the posterior side of the neck (left side shown in FIG. 1(a)) when the tool is worn and a pair of jaw retainers 3a and 3b that extend from both ends of the main body 2 in the same direction (right side shown in FIG. 1(a)).

The pair of jaw retainers 3a and 3b are formed spaced apart by a distance equivalent tithe diameter of the neck and formed into a bent shape so as to come into close contact with the outer periphery of the neck along contours of the lower jaw when the tool is worn. The jaw retainers 3a and 3b are comprised of a restorable member that is deformable to an extent that it does not pose an impediment when the user tosses and turns. A pair of jaw contact portions 4a and 4b are formed into a shape complementary to the bent shape of the lower jaw in the respective jaw retainers 3a and 3b, and the respective jaw contact portions 4a and 4b come into contact with both sides of the lower jaw when the tool is worn. That is, regions of the jaw retainers 3a and 3b at their roots in the main body 2 are thick and regions corresponding to the jaw contact portions 4a and 4b contacting the lower jaw are made to be one step lower so as to have a shape that follows the bent shapes of the lower jaw. The one-step lower regions of the jaw contact portions 4a and 4b are preferably formed with roundness to allow the user to change the orientation of the body such as tossing and turning without imposing a burden on the lower jaw even when the posture is changed from a supine posture (face-up position) to a lateral position. As will be described later, in the supine posture, the jaw contact portions 4a and 4b come into contact with the lower jaw, thereby cause forces received from the main body 2 to directly and reliably act on the lower jaw so as to retain the lower jaw at a height (angle) at which the respiratory tract can be managed.

As shown in FIG. 1(a), the jaw retainers 3a and 3b have built-in support members 5a and 5b that support the lower jaws as to push up the lower jaw from below in some areas that come into contact with the lower jaw when the tool is worn. The upper sides of the support members 5a and 5b constitute the jaw contact portions 4a and 4b. A material having predetermined strength that will not be deformed considerably by the lower jaw is selected for the support members 5a and 5b (e.g., polyethylene (PE), high density polyethylene (HDPE), medium density polyethylene (MDPE), low density polyethylene (LDPE), polypropylene (PP), polyvinyl chloride (PVC), polyvinylidene chloride, polystyrene (PS), polyvinyl acetate (PVAc), ABSresin, ASresin, acrylic resin (PMM)). On the other hand, a material having excellent air-permeability, a pleasant texture and certain flexibility is preferably selected for the jaw retainers 3a and 3b in view that the surface thereof comes into contact with the human body (e.g., polyethylene (PE), high density polyethylene (HDPE), medium density polyethylene (MDPE), low density polyethylene (LDPE), polypropylene (PP), polyvinyl chloride (PVC), polyvinylidene chloride, polystyrene (PS), polyvinyl acetate (PVAc), ABSresin, ASresin, acrylic resin (PMM)). In the present embodiment, the main body 2 and jaw retainers 3a and 3b are formed as a single-piece structure, but these components may also be configured as separate pieces.

A receiving face 2a which is a flat surface substantially perpendicular to the extending directions of the jaw retainers 3a and 3b is formed on the rear of the main body 2 (outer surface opposite to the contact surface that contacts the posterior side of the neck). A tabular body 6 protruding from the rear of the main body 2 on both sides is formed as a single piece and the receiving face 2a is formed on the outer surface of the tabular body 6. The main body 2 including the tabular body 6 needs to be rigid enough to receive stress from the underlay surface side such as a resting face or respiratory tract widening tool mat and at the same time resilient (flexible) enough to deform to an extent that it does not pose an impediment when the user tosses and turns, and is preferably formed of an elastic material such as urethane resin, polyethylene (PE), high-density polyethylene (HDPE), medium density polyethylene (MDPE), low density polyethylene (LDPE), polypropylene (PP), polyvinyl chloride (PVC), polyvinylidene chloride, polystyrene (PS), polyvinyl acetate (PVAc), ABSresin, ASresin, acrylic resin (PMM). This receiving face 2a is placed face down during a supine posture and acts as a surface that receives an upward counterforce from the underlay surface side. That is, in the supine posture, the receiving face 2a presses, for example, the top surface of the respiratory tract widening tool mat which becomes the underlay surface, and thereby receives a counterforce from the top surface side. To efficiently receive the counterforce from the underlay surface side, it is preferable that the area of the receiving face 2a be sufficiently large and stress act on the pair of jaw retainers 3a and 3b uniformly. Therefore, by adopting the flat receiving face 2a to secure a sufficient area, both sides of the lower jaw have substantially the same height without one of the lower jaw being inclined in the supine posture and the lower jaw is retained at a height (angle) at which the respiratory tract is managed. On the other hand, when the posture is changed from the supine posture to a lateral position or prone posture, the main body 2 deforms in response to the change in posture to accept a free posture change. Furthermore, when the posture is returned to the supine posture, the main body 2 receives an upward external force as described above, applies this external force to the respective jaw retainers 3a and 3b, retains the lower jaw at a height at which the respiratory tract can be managed and can thereby automatically manage the respiratory tract.

Furthermore, as shown in FIG. 1(b), a protruding section 7 is provided at a bottom end of the receiving face 2a on the rear of the main body 2. The protruding section 7 extends in a direction opposite to the extending direction of the jaw retainers 3a and 3b and in the downward direction in the supine posture. The protruding section 7 is formed in a substantially semi-circular shape. A thickness T of the protruding section 7 is set to be greater than a width W of a groove formed in the respiratory tract widening tool mat which will be described later. This protruding section 7 comes into contact with the respiratory tract widening tool matin the supine posture and applies stress in the direction in which the lower jaws pushed up to the main body 2. That is, the protruding section 7 that comes into contact with the respiratory tract widening tool mat acts, as a fulcrum, so as to incline the direction in which the lower jaw is pushed up from the directly upward direction to the parietal region side (vertex of the head seen from the distal end of the jaw) and stretch the bent portion of the respiratory tract in a substantially rectilinear shape.

Next, the respiratory tract widening tool mat will be described.

Figure 2:
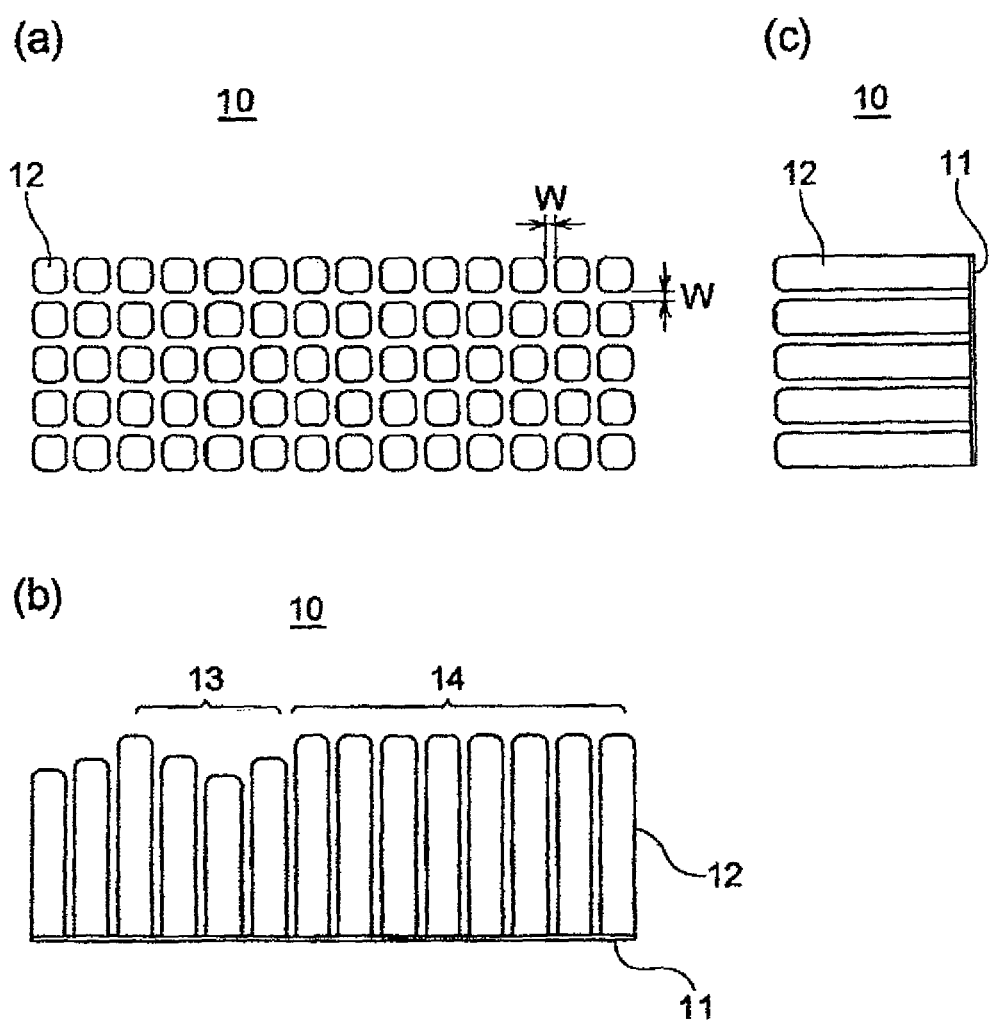
FIG. 2 is a schematic view illustrating a respiratory tract widening tool mat according to the present embodiment, (a) is a top view thereof, (b) is a side view seen from the long side and (c) is a side view seen from the short side.

FIGS. 2(a) to (c) are a top view, side view and side view of the respiratory tract widening tool mat respectively. A respiratory tract widening tool mat 10 is used underlaid beneath the head (including the vicinity of the neck wearing the respiratory tract widening tool 1) in a supine posture.

As shown in FIG. 2(a), the respiratory tract widening tool mat 10 is configured such that a plurality of columnar bodies 12 are vertically arranged in a grid-like array on the top surface of a rectangular substrate 11. The plurality of columnar bodies 12 are made of an elastic material having resilience whereby each columnar body 12 is deformed (depressed) when an external force is applied, whereas each columnar body 12 is returned to the original shape when the external force is removed. A low-resilience sponge material such as urethane resin is suitable as the resilient elastic material. This allows the columnar bodies 12 in a region with which the head comes into contact in the supine posture (hereinafter referred to as "head contacting section") 13 and the columnar bodies 12 in a region with which the receiving face 2a of the respiratory tract widening tool 1 comes into contact in the supine posture (hereinafter referred to as "tool contacting section") 14 to separate from each other and support the head and receiving face 2a independently of each other. Therefore, in the supine posture, when the head and the receiving face 2a of the respiratory tract widening tool 1 come into contact with the respiratory tract widening tool mat 10, the columnar bodies 12 with which the head comes into contact by the weight of the head itself sink deeper than the columnar bodies 12 with which the receiving face 2a comes into contact. This causes the region of the head contacting section 13 to be reliably distinguished from the region of the tool contacting section 14, and the sinking of the respiratory tract widening tool 1 accompanying the sinking of the head in the supine posture is thereby suppressed and the respiratory tract widening tool 1 is supported in a stable state. Therefore, it is possible to reliably transmit an upward counterforce from the top surface of the respiratory tract widening tool mat 10 to the receiving face 2a and retain the lower jaw at a height that allows the jaw retainers 3a and 3b to manage the respiratory tract. On the other hand, when the posture is changed from the supine posture to, for example, a lateral position, the columnar bodies 12 with which the main body 2 and jaw retainers 3a and 3b of the respiratory tract widening tool 1 come into contact deform (depressed) according tithe change in posture, and the user can thereby freely and easily change the body position such as tossing and turning without the change in posture being obstructed. Furthermore, the width W of the grid-like arrayed columnar bodies 12 is formed to be smaller than the thickness T of the protruding section 7 so that the protruding section 7 neither comes into contact with the columnar bodies 12 in the supine posture nor enters the groove.

In the present embodiment, the respiratory tract widening tool mat 10 is formed of the columnar bodies 12, but the present invention is not limited to this, and the respiratory tract widening tool mat 10 may also be formed of, for example, uni-directionally consecutive convex bodies or flat elastic bodies in which no grooves are formed. Furthermore, the respiratory tract widening tool mat 10 may also be constructed of a bag-shaped body filled with a gas, liquid or gel substance. In this case, when the head and respiratory tract widening tool 1 (receiving face 2a) come into contact with the respiratory tract widening tool mat 10, the head sinks deeper than the respiratory tract widening tool 1 due to the difference between respective weights, but the volume of the bag-shaped body itself does not change, and therefore the sinking of the respiratory tract widening tool 1 (receiving face 2a) is suppressed to an extent that the head sinks deeper. Therefore, in the supine posture, the head naturally descends and the respiratory tract widening tool 1 pushes up the lower jaw that receives an upward counterforce from the bag-shaped body and it is thereby possible to manage the respiratory tract.

As shown in FIG. 2(b), in the respiratory tract widening tool mat 10, the head contacting section 13 is formed in a concave shape in which the surface of contact with the head is caved downward. That is, the head contacting section 13 is formed into a shape substantially complementary to the occipital region. On the other hand, the tool contacting section 14 has no caves like the head contacting section 13 and is kept at a fixed height. Thus, the respiratory tract widening tool mat 10 is configured such that the head contacting section 13 is lower than the tool contacting section 14 in the supine posture. To be more specific, the height of the columnar bodies 12 vertically arranged in the head contacting section 13 are set to be lower than the columnar bodies vertically arranged in the tool contacting section 14. Since the columnar bodies 12 of the head contacting section 13 and those of the tool contacting section 14 are independent of each other, when the user lies in a supine posture over the head contacting section 13 and the tool contacting section 14, the respiratory tract widening tool 1 which has been pushed relatively upward pushes up the lower jaw as the head naturally descends, and it is thereby possible to suppress the sinking of the root of tongue and manage the respiratory tract.

Figure 3:
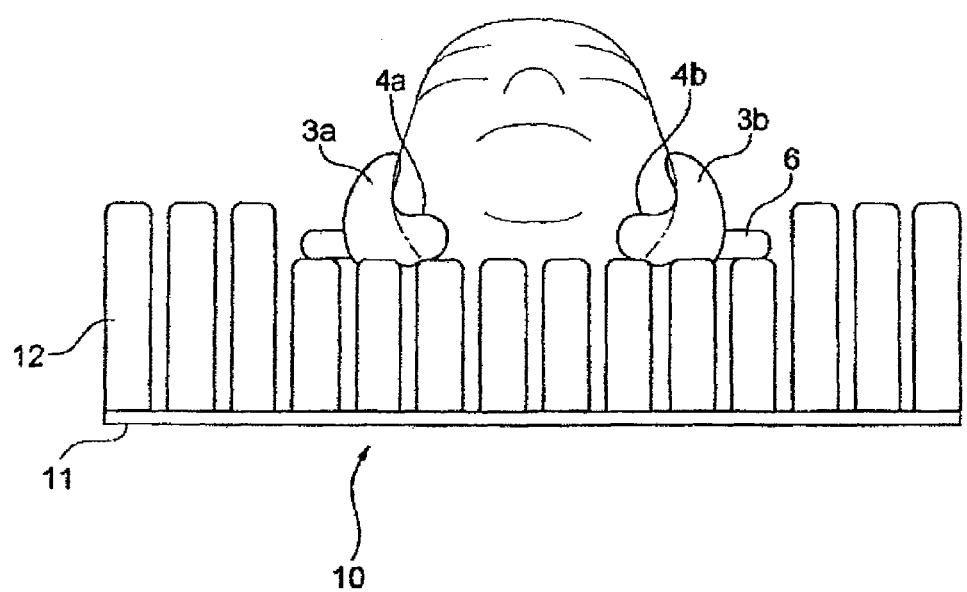
FIG. 3 is a schematic view illustrating a user wearing the respiratory tract widening tool according to the present embodiment lying in a supine posture on a respiratory tract widening tool mat.

Next, operations and effects when the user wearing the respiratory tract widening tool 1 lies in the supine posture on the respiratory tract widening tool mat 10 will be described using FIG. 3 and FIGS. 4(a) and (b). FIG. 3 is a schematic view when the user wearing the respiratory tract widening tool 1 lies in a supine posture on the respiratory tract widening tool mat 10, seen from the direction opposite to the parietal region. Furthermore, FIG. 4(a) shows a condition before the user lies in the supine posture and FIG. 4(b) shows a condition in which the user is lying in the supine posture.

Figure 4:
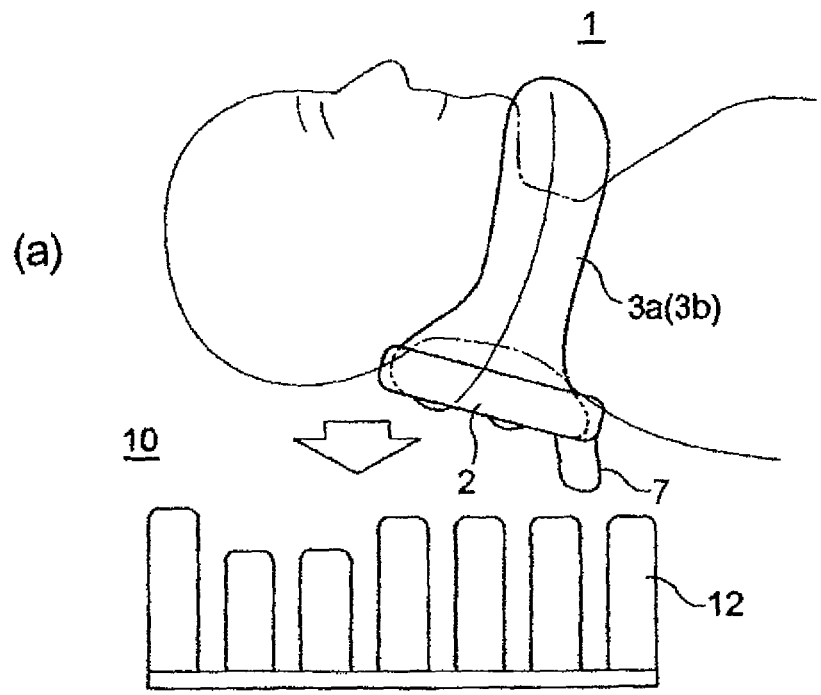
FIG. 4 is a schematic view illustrating a condition of the respiratory tract widening unit according to the present embodiment in a supine posture, (a) is a diagram illustrating the condition before the supine posture and (b) is a diagram illustrating the condition in the supine posture.
Figure 4:
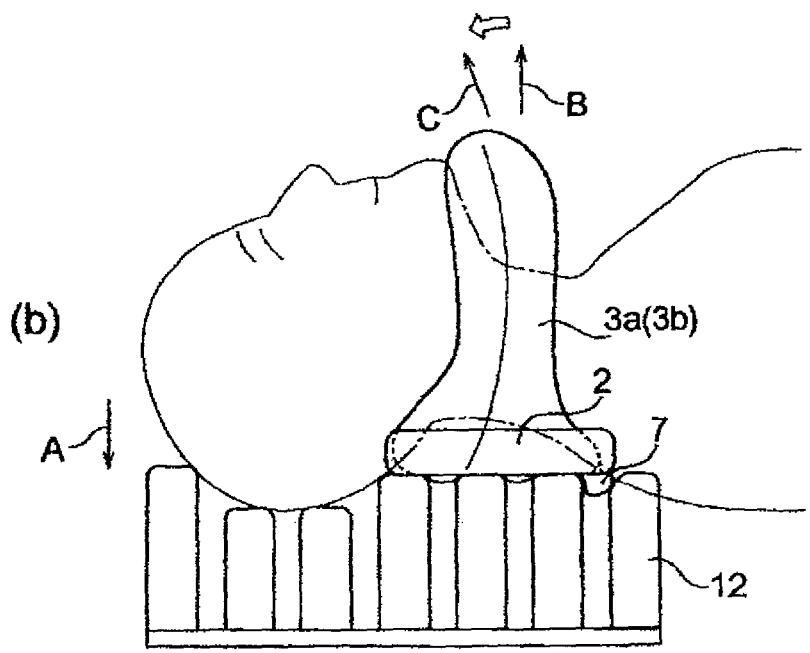

First, as shown in FIG. 3 and FIG. 4(a), the open ends of the jaw retainers 3a and 3b of the respiratory tract widening tool 1 are widened to attach the respiratory tract widening tool 1 from the posterior side of the neck, and the jaw contact portions 4a and 4b are aligned with the positions at which they come into contact with the lower jaw. Then, the user lies in the supine posture so that the occipital region rests on the head contacting section 13 of the respiratory tract widening tool mat 10 placed on a resting surface or a mattress or the like. At this time, the receiving face 2a of the main body 2 of the respiratory tract widening tool 1 comes into contact with the tool contacting section 14 of the respiratory tract widening tool mat 10 which becomes the underlay surface. As shown in FIG. 4(b), when the user sleeps on the respiratory tract widening tool mat 10 in a condition in which the receiving face 2a is aligned with the tool contacting section 14, the occipital region naturally descends (direction indicated by an arrow A), while the receiving face 2a receives a counterforce from the surface of contact with the tool contacting section 14. The greater the area of the receiving face 2a, the greater is the upward counterforce received from the respiratory tract widening tool mat 10, and the sinking of the main body 2 of the respiratory tract widening tool 1 is suppressed.

Furthermore, the thicker the main body 2, the greater is the upward force that the main body 2 of the respiratory tract widening tool 1 received from the respiratory tract widening tool mat 10. Thus, the main body 2 of the respiratory tract widening tool 1 is prevented from sinking, the main body 2 corresponding tithe posterior side of the neck is pushed up (direction shown by a narrow B) by the force received from the tool contacting section 14 of the respiratory tract widening tool mat 10 with the jaw contact portions 4a and 4b being in contact with the lower jaw, the support members 5a and 5b push up the lower jaw from below retaining the lower jaw at a height at which the respiratory tract can be managed. At this time, the protruding section 7 of the respiratory tract widening tool 1 comes into contact with the columnar bodies 12 of the respiratory tract widening tool unit 10 so as to press the columnar bodies 12, and the jaw retainers 3a and 3b (support members 5a and 5b) are thereby retained while pushing up the lower jaw in the direction toward the parietal region side (direction shown by an arrow C) via the main body 2. Thus, it is possible to more reliably prevent the sinking of the root of tongue and manage the respiratory tract.

On the other hand, when the posture is changed from the supine posture shown in FIG. 4(b) to a lateral position or the like, the main body 2 and jaw retainers 3a and 3b deform in response to the change in posture. This allows the user to freely change the posture from the face-up position such as tossing and turning. When the posture is changed from the face-up position to lateral position, the root of tongue does not sink into the throat, and therefore the respiratory tract is managed without being closed, thus eliminating the necessity for retaining the lower jaw at a height at which the respiratory tract can be managed. When the face-up position is restored from the lateral position, the main body 2 and jaw retainers 3a and 3b deform in response to the change in posture and the jaw retainers 3a and 3b (support members 5a and 5b) receive stress in the directions shown by the arrows B and C from the respiratory tract widening tool mat 10 via the main body 2 again. This causes the jaw contact portions 4a and 4b to support the lower jaw from below to a height at which the respiratory tract can be managed, thus enabling the respiratory tract to be automatically managed.

By the way, sleep can be classified into REM sleep which is such a shallow sleep state as to have a dream and non-REM sleep which is such a deep sleep state as to have no dream. During sleep of a healthy person, REM sleep and non-REM sleep alternate in cycles of approximately 90 minutes. Sleep apnea or snoring is likely to occur in the case of non-REM sleep and is caused by the front wall of the respiratory tract of the throat or the root of tongue sinking and thereby narrowing or closing the respiratory tract. When sleep apnea or the like occurs, the sleep state is changed from non-REM sleep to REM sleep, and one can no longer obtain deep sleep no matter how much one sleeps, unable to obtain deep sleep or rest one's brain. Furthermore, during non-REM sleep, daily required human growth hormone is secreted from the anterior pituitary in the brain. This human growth hormone is important forth growth and maintenance of muscles and bones or to induce the repair of the stomach and intestines or skin, and in the case where non-REM sleep lasts shorter than a predetermined period, the hormone is not sufficiently secreted and muscle or the like cannot recover from fatigue either.

According to the present embodiment, the main body 2 of the respiratory tract widening tool 1 receives an upward force in the supine posture, the pair of jaw retainers 3a and 3b extending from the main body 2 come into contact with the opposite sides of the lower jaw and retain the lower jaw at a height at which the respiratory tract can be managed to thereby prevent the root of tongue contacting the lower jaw (bone) from falling into the throat side. That is, in the supine posture, the upward force received by the main body 2 is made to act on the jaw retainers 3a and 3b (support members 5a and 5b) to retain the height of the lower jaw so that the height of the sub maxilla is not lowered due to relaxation or the like of the neck muscle during sleep (deep sleep). On the other hand, the main body 2 and the jaw retainers 3a and 3b are made of a restorable member and the respiratory tract widening tool 1 has a structure independent of a pillow or the like, and therefore when the posture is changed from the supine posture to a lateral position or prone posture, the main body 2 and the jaw retainers 3a and 3b freely deform in conformity with the changed posture. This prevents the root of tongue contacting the sub maxilla from falling into the throat side, and can thereby manage the respiratory tract and allows the user to freely change the posture from the supine posture such as tossing and turning. Furthermore, when the supine posture is restored, the main body 2 receives the upward force and the jaw retainers 3a and 3b (support members 5a and 5b) retain the lower jaw at a height at which the respiratory tract can be managed, and it is thereby possible to automatically manage the respiratory tract without disturbing comfortable sleeping. Particularly, the respiratory tract widening unit according tithe present embodiment doubtfully has a great effect in enabling smooth breathing of sleep apnea patients and keeps the aforementioned regular sleep pattern, and thereby has a noticeable effect from the standpoint of health maintenance as well.

Figure 5:
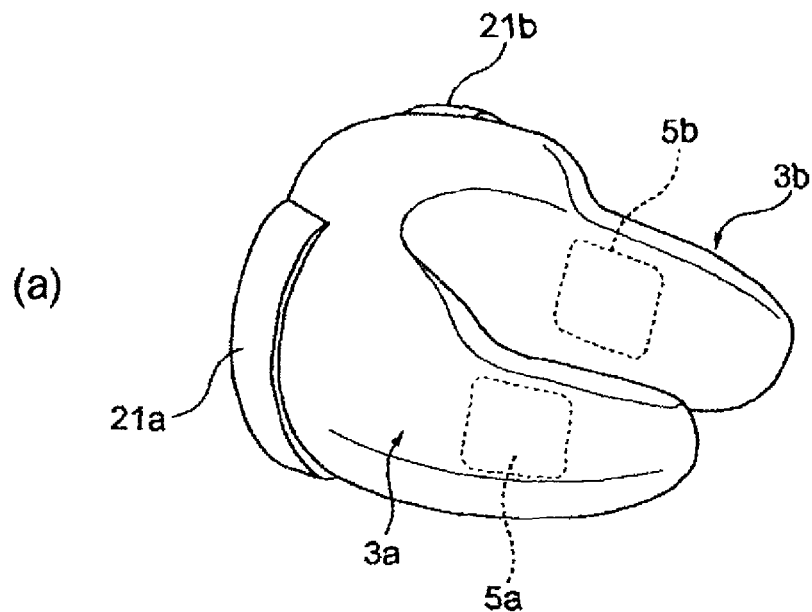
FIG. 5 is a schematic view illustrating respiratory tract widening tool according to a modification example.
Figure 5:
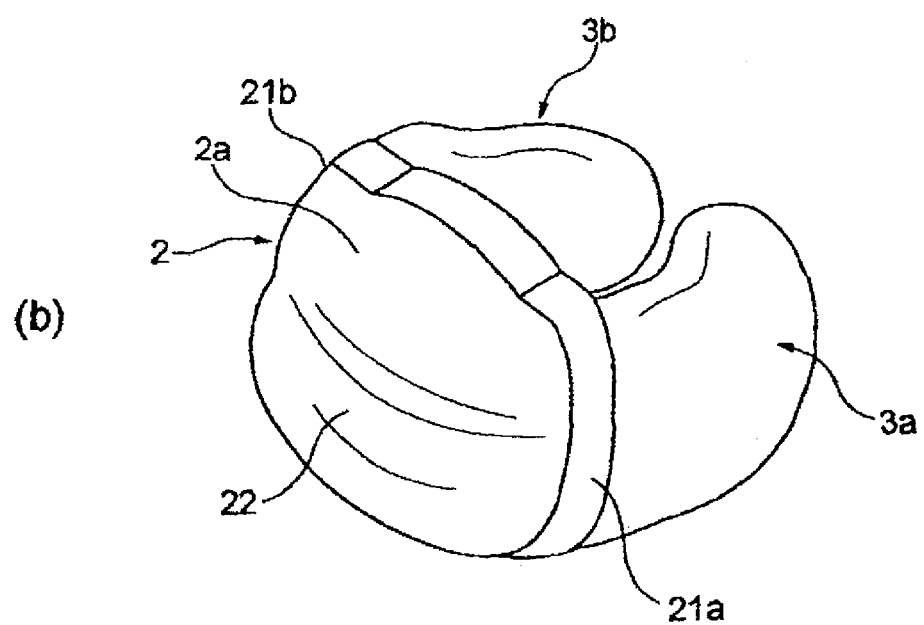

The above embodiment makes the main body 2 extend on both sides to secure a sufficient area of the receiving face 2a, but the shape of the main body 2 is not limited to this. For example, as shown in FIG. 5, protruding sections 21a and 21b that protrude from the rear of the main body 2 toward both sides may have a small size and have an accurately bent shape instead of a completely flat shape. Furthermore, the protruding section formed at the bottom of the receiving face 2a may also be a falcate protruding section 22 along the rear of the accurately bent main body 2 as shown in FIG. 5. Thus, even when the rear of the main body 2 is not completely flat, the main body 2 can receive sufficiently strong stress from the underlay surface side in the supine position, and push up the lower jaw to a height that allows the jaw retainers 3a and 3b to manage the respiratory tract.

As shown in FIG. 5, when the falcate protruding section 22 is provided along the rear of the accurately bent main body 2, even if the respiratory tract widening tool mat 10 is not used, the protruding section 22 that directly comes into contact with the resting surface in the supine posture applies the force received from the resting surface to the jaw retainers 3a and 3b, and can thereby push up and retain the lower jaw.

Furthermore, adjusting means such as a hook, magic tape (registered trademark) may be provided on the open end side of the pair of jaw retainers 3a and 3b. This makes it possible to adjust the mounting state of the respiratory tract widening tool 1 so as to reliably manage the respiratory tract in the supine posture according to the size and shape of the human face and lower jaw.

Furthermore, the above embodiment forms the head contacting section 13 of the respiratory tract widening tool mat 10 so as to be lower than the tool contacting section 14, but the present invention is not limited to this, and the head contacting section 13 and the tool contacting section 14 may be configured to have the same height. That is, the present invention is applicable even when the height of the columnar bodies 12 vertically arranged in the head contacting section 13 is equal to the height of the columnar bodies 12 vertically arranged in the tool contacting section 14. In this case, as opposed to the case where the occipital region sinks into the head contacting section 13 by the self-weight in the supine posture, the receiving face 2a of the main body 2 comes into contact with the contact surface of the tool contacting section 14 to prevent the respiratory tract widening tool 1 from sinking together along with the sinking of the head and causes the counterforce received from the contact surface to act on the main body 2.

Second Embodiment

Next, a second embodiment of the present invention will be described. A respiratory tract widening tool according to the second embodiment of the present inventions different from the respiratory tract widening tool 1 according to the aforementioned first embodiment only in the configuration of the main body and jaw retainers. Therefore, the present embodiment will only describe differences in particular, and identical components will be assigned the same reference numerals and overlapping explanations will be omitted.

Figure 6:
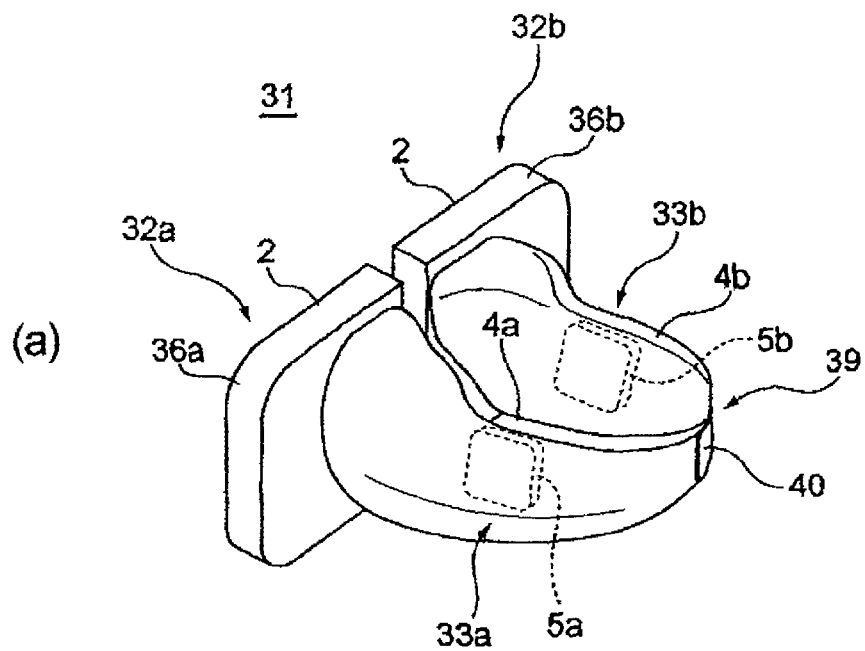
FIG. 6 is an outside perspective view schematically illustrating respiratory tract widening tool according to a second embodiment of the present invention, (a) is an outside perspective view seen from the front and (b) is an outside perspective view seen from thereof.
Figure 6:
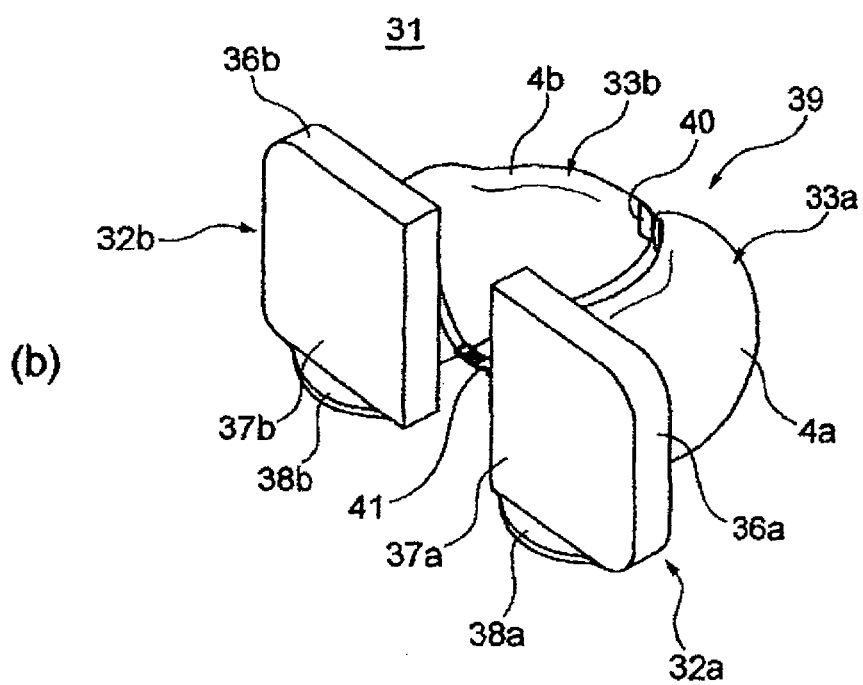

FIGS. 6(a) and (b) are outside perspective views of the respiratory tract widening tool according to the present embodiment. The respiratory tract widening tool 31 shown in FIG. 6 is provided withal first main body 32a and a second main body 32b configured as separate bodies, and jaw retainers 33a and 33b configured as separate bodies and connected to the main bodies 32a and 32b respectively.

The first main body 32a is integrally formed as a single piece with a tabular body 36a that protrudes on both sides and one jaw retainer 33a extends from the front of the main body 32a. Similarly, the second main body 32b is integrally formed as a single piece with a tabular body 36b that protrudes on both sides and the other jaw retainer 33b extends from the front of the main body 32b. Receiving faces 37a and 37b which form flat surfaces substantially perpendicular to the extending direction of the jaw retainers 33a and 33b are formed on the rear of the main bodies 32a and 32b respectively and protruding sections 38a and 38b are provided at the bottom end of the receiving faces 37a and 37b respectively. It is preferable to provide the protruding sections 38a and 38b since the protruding sections 38a and 38b act to cause the protruding direction of the lower jaw to incline from the directly upward direction toward the parietal region side so as to stretch the bent portion of the respiratory tract substantially rectilinearly. However, even in a configuration without the protruding sections 38a and 38b, it is also possible to cause external forces received by the receiving faces 37a and 37b in the supine posture to act on the respective jaw retainers 33a and 33b to retain the lower jaw at a height at which the respiratory tract can be managed.

Furthermore, adjusting means 39 for adjusting wearing positions of both sides of the lower jaw of the jaw retainers 33a and 33b is provided between the pair of jaw retainers 33a and 33b. The adjusting means 39 is made up of a hinge (or hook) 40 provided so as to couple distal end sides of the jaw retainers 33a and 33b, and an adjusting belt 41 provided so as to bridge between the opposed rear ends of the jaw retainers 33a and 33b. When the respiratory tract widening tool 31 is worn, the jaw retainers 33a and 33b are coupled together by the hinge 40, the respiratory tract widening tool 31 is positioned with the lower jaw contact portions 4a and 4b of the respective jaw retainers 33a and 33b placed in close contact with the outer periphery of the neck along the contours of both sides of the lower jaw in such a way that the receiving faces 37a and 37b substantially uniformly receive an external force in the supine posture, and fixed on the occipital region side using the adjusting belt 41. Thus, even when the posture is changed from the supine posture and restored to the supine posture again, it is possible to cause the upward force received by the receiving faces 37a and 37b of the main bodies 32a and 32b to act on the jaw retainers 33a and 33b appropriately and retain the lower jaw at a height at which the respiratory tract can be managed.

Thus, according to the present embodiment, since the main bodies 37a and 37b connected to the jaw retainers 33a and 33b are configured as separate bodies, in addition to the effects of the above-described first embodiment, the present embodiment allows the user to change the posture such as tossing and turning more easily. Furthermore, the wearing positions of the jaw retainers 33a and 33b with respect to the lower jaw are adjusted according to the shape or the like of the lower jaw, and therefore even when the posture is restored to the supine posture after tossing and turning, for example, it is possible to suppress deviation of the contact position of the jaw retainers 33a and 33b with respect to the lower jaw and appropriately retain the lower jaw at a height at which the respiratory tract can be managed.

The present invention is not limited to the above-described embodiments, but can be implemented modified in various ways. The size and shape or the like of the above-described embodiments are not limited to those illustrated in the attached drawings, but can be modified as appropriate within a range in which the effects of the present invention can be exerted. Other aspects can be implemented modified as appropriate without departing from the scope of objects of the present invention.

The present invention is useful for treatment of sleep apnea in the medical field and health maintenance in daily life.

What is claimed is:

1. A respiratory tract widening tool for attaching to an outer periphery of a human neck, comprising:
    a main body that comes into contact with a posterior side of the neck when the tool is worn and receives an upward external force in a supine posture;
    a pair of jaw retainers that extend forward from the main body spaced apart by a distance equivalent to a diameter of the neck and come into contact with both sides of a lower jaw when the tool is worn; and
    a protruding section that is provided in the main body and applies stress in a direction of pushing up the lower jaw in a supine posture to the main body, wherein:
    the main body and the pair of jaw retainers are formed of a restorable member,
    the pair of jaw retainers have jaw contact portions respectively, which are formed into a shape complementary to a bent shape of the lower jaw and come into contact with the lower jaw to support the lower jaw from below,
    the main body and jaw retainers deform, when the posture is changed from the supine posture, in conformity with the posture, and when the posture is changed to the supine posture, the external force received by the main body is made to act on jaw contact portions to push up the lower jaw and retain the lower jaw at a height at which the respiratory tract can be managed, and
    the main body comprises a receiving face that is directed downward in a supine posture to press a tool underlay surface facing the neck and also receives a counterforce from the underlay surface.

2. A respiratory tract widening tool for attaching to an outer periphery of a human neck, comprising:
    a main body that comes into contact with a posterior side of the neck when the tool is worn and receives an upward external force in a supine posture; and
    a pair of jaw retainers that extend forward from the main body spaced apart by a distance equivalent to a diameter of the neck and come into contact with both sides of a lower jaw when the tool is worn, wherein:

the main body and the pair of jaw retainers are formed of a restorable member, the main body and jaw retainers deform, when the posture is changed from the supine posture, in conformity with the posture, and when the posture is changed to the supine posture, an external force received by the main body is made to act on the jaw retainers to retain the lower jaw at a height at which the respiratory tract can be managed, the main body comprises a first main body that is connected to one of the jaw retainers and a second main body that is configured as a body independent of the first main body and connected to the other jaw retainer, and the pair of jaw retainers comprises adjusting means for adjusting an attaching position of the jaw retainers connected to the first and second main bodies with respect to both sides of the lower jaw.

3. A respiratory tract widening unit comprising:
the respiratory tract widening tool according to claim 1; and
a respiratory tract widening tool mat underlaid beneath the respiratory tract widening tool, wherein:
a head contacting section of the respiratory tract widening tool mat with which the head comes into contact in a supine posture is lower than a tool contacting section with which the main body of the respiratory tract widening tool comes into contact in the supine posture, and
the respiratory tract widening tool mat comprises a plurality of columnar bodies that are formed of a restorable elastic material and the columnar bodies vertically arranged in the head contacting section are lower than the columnar bodies vertically arranged in the tool contacting section.

4. The respiratory tract widening unit according to claim 3, wherein the elastic material is made of urethane resin.

5. The respiratory tract widening unit according to claim 3, wherein the respiratory tract widening tool mat is made up of a bag-shaped body filled with a gas, liquid or gel substance.

6. A respiratory tract widening unit comprising:
the respiratory tract widening tool according to claim 2; and
a respiratory tract widening tool mat underlaid beneath the respiratory tract widening tool, wherein:
a head contacting section of the respiratory tract widening tool mat with which the head comes into contact in a supine posture is lower than a tool contacting section with which the main body of the respiratory tract widening tool comes into contact in the supine posture, and
the respiratory tract widening tool mat comprises a plurality of columnar bodies that are formed of a restorable elastic material and the columnar bodies vertically arranged in the head contacting section are lower than the columnar bodies vertically arranged in the tool contacting section.

7. The respiratory tract widening unit according to claim 6, wherein the elastic material is made of urethane resin.

8. The respiratory tract widening unit according to claim 6, wherein the respiratory tract widening tool mat is made up of a bag-shaped body filled with a gas, liquid or gel substance.

* * * * *